United States Patent [19]
Denis et al.

[11] Patent Number: 5,973,197
[45] Date of Patent: Oct. 26, 1999

[54] PROCESS FOR THE PREPARATION OF CARBOXYLIC ACIDS BY CARBONYLATION IN THE PRESENCE OF RHODIUM

[75] Inventors: Philippe Denis, Decines; Robert Perron, Charly; Joel Schwartz, Caluire, all of France

[73] Assignee: BP Chemicals Limited, London, United Kingdom

[21] Appl. No.: 08/836,817

[22] Filed: Apr. 21, 1997

Related U.S. Application Data

[63] Continuation of application No. PCT/FR95/01447, Nov. 3, 1995.

[30] Foreign Application Priority Data

Nov. 4, 1994 [FR] France .................................. 94 13176

[51] Int. Cl.$^6$ .................................................. C07C 51/12
[52] U.S. Cl. .................................................. 562/519
[58] Field of Search ............................................. 562/519

[56] References Cited

U.S. PATENT DOCUMENTS 4,733,006 3/1988 Singleton et al. ...................... 562/519
5,237,097 8/1993 Smith et al. ............................ 562/519

Primary Examiner—Paul J. Killos
Assistant Examiner—J. Parsa
Attorney, Agent, or Firm—Fay, Sharpe, Beall, Fagan, Minnich & McKee

[57] ABSTRACT

A method for preparing carboxylic acids by carbonylating a reagent, particularly an alcohol, in the presence of a rhodium catalyst. According to the method, the liquid phase reaction is carried out in a first zone in the presence of a rhodium catalyst, and the resulting reaction mixture is partially vaporised in a second zone. The vaporised fraction containing the carboxylic acid is later purified and the unvaporised liquid fraction containing the catalyst is recirculated to the first zone. The method is charactracterised in that said unvaporised fraction is contacted with carbon monoxide in such a way that this compound is not returned to the second zone.

14 Claims, 3 Drawing Sheets

PROCESS FOR THE PREPARATION OF CARBOXYLIC ACIDS BY CARBONYLATION IN THE PRESENCE OF RHODIUM

This application is a continuation of co-pending International application No. PCT/FR95/01447 filed on Nov. 3, 1995, and claims foreign priority France 94/13176 filed Nov. 4, 1994.

The object of the present invention is a process for the preparation of carboxylic acids by carbonylation of a reagent, chosen notably from among the alcohols, in the presence of a catalyst based on rhodium.

Carbonylation processes using soluble catalysts based on rhodium for the preparation of carboxylic acids are known processes. They are in general used in installations essentially comprising three zones. The first zone corresponds to the reaction zone proper, comprising a pressurised reactor in which the carbonylation takes place. The second zone consists of a zone for separating the acid formed. This operation is formed by partial vaporization of the reaction mixture in a unit (called a flash unit) in which the pressure is kept lower than in the reactor. The vaporised portion is then directed to a third zone in which the carboxylic acid produced is purified. This zone comprises various distillation columns in which the carboxylic acid produced is separated from the water, the reagents and the byproducts. The portion of the mixture which remains in liquid form at the outlet of the vaporization zone and includes notably the catalyst is recycled to the reactor. This is conventionally achieved by means of a pump.

On the occasion of implementing this type of process, a catalyst stability problem has had to be faced. It has more particularly been observed that the catalyst precipitates in the zone of partial vaporization of the reaction mixture.

Several solutions have therefore been envisaged for solving this problem.

The first solution suggested was to maintain a high water content in the reactor, in the region of 14 to 15%. However, this solution is not advantageous from an economic point of view. The increase in the water content in the reaction medium has the consequence, in fact, of increasing the cost of the subsequent separation of the acid produced and the water.

The second solution envisaged amounts to introducing an element into the reaction mixture in order to stabilize the catalyst. These stabilizing agents are in particular chosen from among alkaline metal iodides such as lithium iodide or else potassium iodide, or else chosen from among organic compounds capable of forming ionic species with the iodine present in the medium, such as organonitrogen or organophosphorus compounds. Compounds of the alkaline iodide type are in fact the preferred elements, since they are used almost systematically in carbonylation processes. In fact, the addition of these compounds has made it possible to lower the water content in the reactor and hence render such processes more competitive compared with the previous ones described.

Another type of solution has been proposed, consisting in introducing carbon monoxide into the zone of partial vaporization of the reaction mixture so that the partial pressure of this gas in said zone is not more than 2 bar. The carbon monoxide is introduced in the form of a pure or diluted gas which is bubbled into the liquid fraction situated in the bottom of the vessel in which the separation by partial vaporization of the reaction mixture is effected. This process presents several disadvantages. First of all, an inevitable loss of carbon monoxide takes place. In fact, in order to maintain a partial pressure of carbon monoxide of this order in the flash unit, where the total pressure is also relatively low, it is necessary to mobilize very substantial carbon monoxide flows. Moreover, carbon monoxide solubilization can only be obtained effectively in the presence of vigorous agitation. A flash unit, however, includes no such means. This has the consequence that the major part of the carbon monoxide flow will escape with the vaporised fraction of the reaction medium. There are two alternatives at this stage. Either the gas is destroyed, which is not permissible, since the amount lost is very large and this gas is one of the reagents in the carbonylation reaction. Or the gas is recycled, but this causes a far from negligible extra cost because it is necessary to separate this gas from the gaseous by-products of the reaction, which are notably hydrogen, methane and carbon dioxide. In addition, the fact of mobilizing such substantial flows may have consequences at the level of the installation itself, notably as regards the size of the vessels.

The object of the present invention is therefore a process for the preparation of carboxylic acids by carbonylation in the presence of a catalyst based on rhodium, in which the stabilization of the catalyst is carried out in a simple and effective manner.

The process according to the invention may also permit the content of agents stabilising the catalyst and the water content to be reduced.

Moreover, the process according to the invention prevents any unnecessary loss of carbon monoxide.

Thus the process for the preparation of carboxylic acids according to the invention consists in effecting, in a first zone, the liquid phase reaction in the presence of a rhodium based catalyst, followed, in a second zone, by partially vaporizing the reaction mixture obtained; the vaporized fraction, including the carboxylic acid produced, is subsequently purified and the non-vaporized liquid fraction, including the catalyst, is recycled to the first zone. The characteristic of the process is that the non-vaporized liquid fraction from the second zone is placed in contact with carbon monoxide in such a way that this compound does not return to the second zone.

BRIEF DESCRIPTION OF DRAWINGS

However, other advantages and characteristics will appear more clearly on reading the description and the diagrams that follow, for which.

Figure 1:
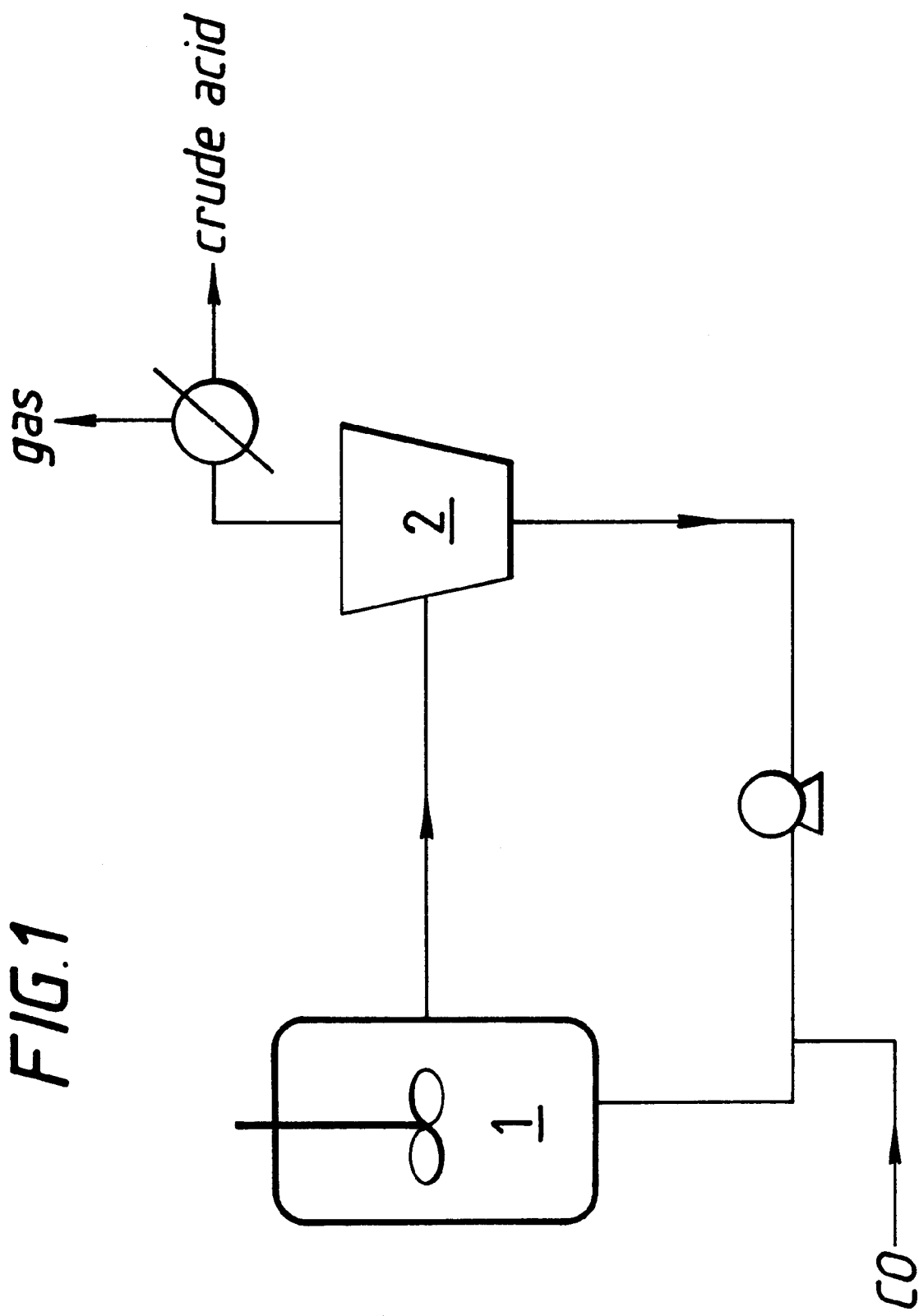
FIG. 1 represents a first embodiment in which the non-vaporized fraction is placed in contact with carbon monoxide in the form of a gas.

The process according to the invention may therefore be used for the preparation of carboxylic acids by carbonylation.

In the ensuing, contents are expressed in percentage by weight save indication to the contrary.

The reagent employed in this type of reaction is generally chosen from among the alcohols. The alcohols suitable for implementing the reaction include alcohols, saturated, mono or dihydroxylated, possessing one to ten carbon atoms. Examples of such compounds include notably methanol, ethanol, propanol, butanol, 1,4-butanediol. Monohydroxylated alcohols are preferred.

It is important to note that the alcohol may be present in the reaction medium as such or in a masked form. It may in fact be present indiscriminately in the form of a halogenated derivative and/or an ether and/or an ester obtained by reaction between said alcohol and the carboxylic acid present.

The reaction takes place in the presence of a catalytic system comprising on the one hand a soluble species of rhodium and on the other hand a halogenated promoter.

The rhodium based compounds used are generally chosen from among the coordination complexes of this metal which are soluble in the medium, under the reaction conditions. More particularly, coordination complexes are used whose ligands are on the one hand carbon monoxide and on the other a halogen which is more particularly iodine. It is naturally possible to use soluble complexes based on organic ligands. By way of rhodium based compounds, reference may notably be made to U.S. Pat. No. 3,769,329, which gives an indicative list of them.

With regard to the promoter, it corresponds more particularly to the halogenated form of the aforesaid alcohol. For preference, the halogen is iodine.

The content of halogenated promoter is generally kept between 5 and 20%.

The carbonylation is also effected in the presence of the ester corresponding to the alcohol and to the acid made.

More particularly, the ester content is between 0.5 and 5%.

The carbonylation reaction is also implemented in the presence of water. The water content may vary within wide limits and be notably between 0 exclusive and 20%. For preference, however, it is less than 10%.

The reaction medium also includes an agent stabilizing the catalyst. This agent is generally chosen from among alkaline metal iodides such as potassium iodide or lithium iodide, although iodides of organic compounds may be considered.

The content of this agent is generally between 2 and 20%. By applying the process according to invention it is possible to lower the amount of iodide required. It is thus possible to consider effecting the reaction in the presence of an amount of iodide as low as of the order of 1%.

Finally, the solvent of the reaction is advantageously the carboxylic acid which it is desired to make.

The carbonylation reaction is conducted at a temperature of between 150 and 250° C.

The total pressure in the reactor is conventionally between 1 and 100 bar absolute.

The carbon monoxide partial pressure in the reactor varies more particularly between 1 and 50 bar absolute.

The carbon monoxide may be introduced into the reactor in a pure form or diluted in a gas such as hydrogen, methane or else nitrogen. The reaction mixture is thereafter treated continuously in the zone for separating the acid formed, in which a fraction of said reaction mixture is vaporized. In this portion the total pressure is more limited than that of the reactor. It is generally between 1 and 20 °bar absolute.

The operation may take place without applying heat to the flash unit (adiabatic conditions) or with added heat. According to a preferred variant, the partial vaporization is effected in an adiabatic flash unit.

As mentioned previously, the vaporized fraction includes the carboxylic acid production, but also the reagents and by-products of the reaction. This vaporized fraction is directed to the acid purification zone, which includes conventionally several distillation columns in which the acid produced is purified.

The non-vaporized liquid fraction, including notably the catalyst, is recovered at the bottom of the flash unit in order to be recycled to the reactor.

The carbonylation process according to the invention therefore consists in placing said non-vaporized fraction in contact with carbon monoxide in such a way that this compound does not return to the second zone, that of partial vaporization of the reaction mixture. When it is said that the introduction of carbon monoxide is such that this compound does not return to the second zone, it is meant that means are employed to prevent this compound being degassed directly to the flash unit.

Without wishing to be limited by any theory whatsoever, it has been found that the catalyst tends to form inactive species, by a relatively slow and reversible process. These species cause the formation of precipitates after several runs through the recycling loop from the separation zone to the reaction zone. The introduction of carbon monoxide into this part of the process, however, without having any return of said compound to the flash zone, makes it possible to reduce the concentration of these inactive species. Consequently the formation of precipitate is, unexpectedly, prevented and the catalyst is reactivated.

According to a first variant of the invention, the carbon monoxide is introduced in the form of a gas.

To prevent said compound returning to the flash unit, it is introduced downstream of the pump which is used for recycling the non-vaporized liquid fraction to the reactor. The carbon monoxide may be employed in a pure form or else include other gases such as hydrogen, methane, nitrogen. For preference, the carbon monoxide used is of sufficient purity to prevent the accumulation of an undue amount of gases which are not active for the carbonylation reaction.

The carbon monoxide partial pressure employed varies within wide limits.

The non-vaporized fraction may also be subjected to any type of treatment, with the object notably of purifying it, such as for example a treatment, which will be detailed hereinunder, for eliminating corrosion metals.

According to a second variant of the present process, the non-vaporized fraction of the reaction mixture from the flash unit is placed in contact with a liquid flow including carbon monoxide in the dissolved state, before being returned to the reactor.

This variant is advantageous in that introducing a liquid in which carbon monoxide is dissolved makes it possible to render this compound active instantaneously.

The carbon monoxide may here again be employed in a pure form or include other gases such as hydrogen, methane, nitrogen. What was stated in this respect in connection with the first variant holds good in this case.

The amount of carbon monoxide introduced is at most equal to the limit of the solubility of this gas in the liquid employed, depending on the temperature and pressure conditions. More particularly the amount of carbon monoxide dissolved is between 0 exclusive and 10%, this content being related to the temperature and pressure of the liquid.

The liquid flow in which the carbon monoxide is dissolved is chosen so as to be compatible with the carbonylation reaction mixture.

According to a first embodiment, the liquid flow in which the carbon monoxide is dissolved consists of carboxylic acid and/or any other reagent employed during the carbonylation. The carboxylic acid, or any other reagent, may be used in a pure form or may advantageously come from the purification zone situated downstream.

According to a second embodiment, the carbon monoxide is dissolved in a solution which also includes the catalyst. According to this embodiment, at least part of the non-vaporized liquid fraction from the separation zone is derived from the recycling loop in order to be placed in contact with the carbon monoxide. The liquid flow thus treated is thereafter brought together with the other portion of the liquid fraction leaving the flash unit. This embodiment is particularly advantageous in that part of the catalyst is treated with the carbon monoxide, thus permitting its reactivation.

According to a particular variant of this second embodiment, the portion of the liquid fraction in which the carbon monoxide is solubilized is treated beforehand on an ion exchange resin in order to eliminate corrosion metals from it. This is performed by any means known to one skilled in the art.

It is thus possible to use more particularly resins of the strong acid type, in a hydrogen form. These resins may be in gel form or else macro-crosslinked.

The placing in contact may be conventionally effected in fixed bed or in fluidised bed.

The temperature at which the treatment is effected has naturally to be suited to the strength of the resin. It is generally between ambient temperature and 100° C.

Whatever the solution in which the carbon monoxide is dissolved is, the gas solubilization operation takes place in a vessel under powerful agitation. Any means whatsoever may be used to achieve such a result, whether they be of a mechanical nature or not.

The temperature of placing in contact is between 25 and 200° C.

The pressure is at least equal to the pressure prevailing in the reactor. More particularly, the pressure is between 1 and 100 bar absolute.

The solution including the dissolved carbon monoxide is introduced into a part of the recycling loop in such a way as to prevent the carbon monoxide being degassed and carried off towards the flash unit and to prevent cavitation of the pump used for returning the liquid fraction from the flash unit to the reactor. One skilled in the art is able, using his/her particular knowledge of chemical engineering, to determine the appropriate area for introducing the solution including the dissolved carbon monoxide.

It should be noted that the degassing of part of the carbon monoxide towards the reactor poses no particular problem, since this compound is consumed in the carbonylation reaction and is therefore not lost with the gaseous byproducts.

It should be noted that it would not be beyond the scope of the present invention to use a combination of the two variants described above, i.e. the placing of the non-vaporized fraction in contact with carbon monoxide dissolved or not dissolved in a liquid flow.

The diagrams will now be described. FIG. 1 describes an embodiment of the first variant, in which the non-vaporized fraction is placed in contact with carbon monoxide in gas form. Thus the carbon monoxide and the alcohol are introduced into the reactor (1) comprising the catalytic system, the carboxylic acid, the ester, the water and the stabilizing agent. At the reactor outlet the pressure of the reaction mixture is reduced by means of a valve (not shown in the diagram), thus causing partial vaporization of the mixture, and is introduced into the flash unit (2). The vaporized fraction is condensed so as to separate the carboxylic acid to be purified from the uncondensable products, namely the carbon monoxide and the gaseous by-products of the reaction. The fraction remaining in liquid form is introduced into the recycling loop to the reactor. The carbon monoxide is introduced downstream of the pump used for recycling the liquid fraction.

Figure 2:
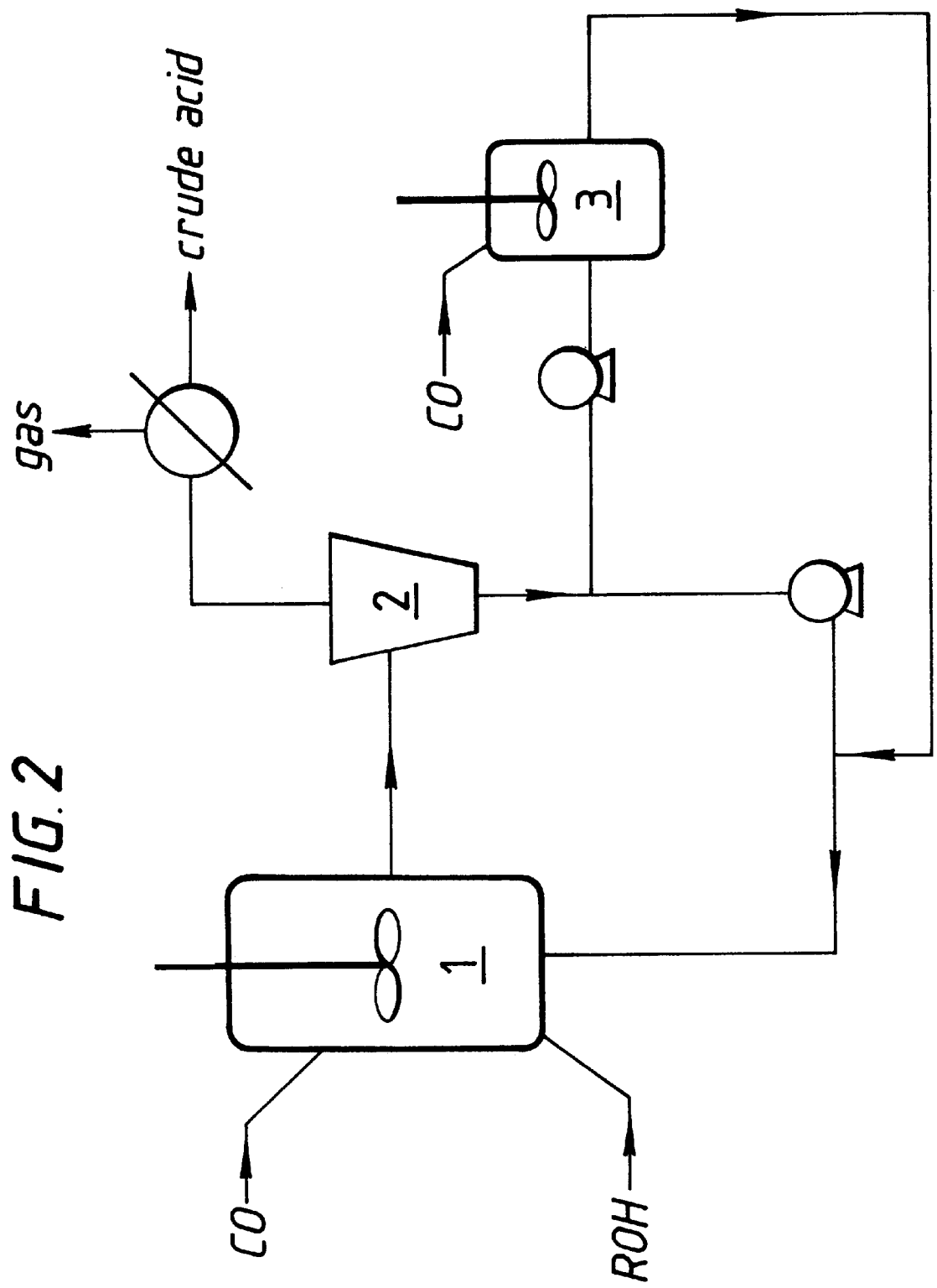
FIG. 2 represents a second embodiment in which carbon monoxide is dissolved in part of the non-vaporized liquid fraction from the flash unit.

FIG. 2 describes an embodiment of the second variant, in which part of the non-vaporized fraction is placed in contact with carbon monoxide dissolved in a liquid flow. Thus the carbonylation reaction takes place as depicted in the foregoing diagram. At the reactor outlet the reaction mixture is introduced into the flash unit (2). The vaporized fraction is condensed in order to separate the carboxylic acid to be purified from the uncondensable products. The fraction remaining in liquid form is introduced into the recycling loop to the reactor. Part of this flow is then diverted from the recycling loop in order to be introduced into a reactor (3) provided with means of agitation and of introducing carbon monoxide. Once the solubilization of this gas has been effected, the liquid enriched with carbon monoxide is brought together with the flow which has not been treated, after having been first, if necessary, subjected to pressure reduction in order to return to a pressure close to that of the reactor, by means of a valve (not shown).

Figure 3:
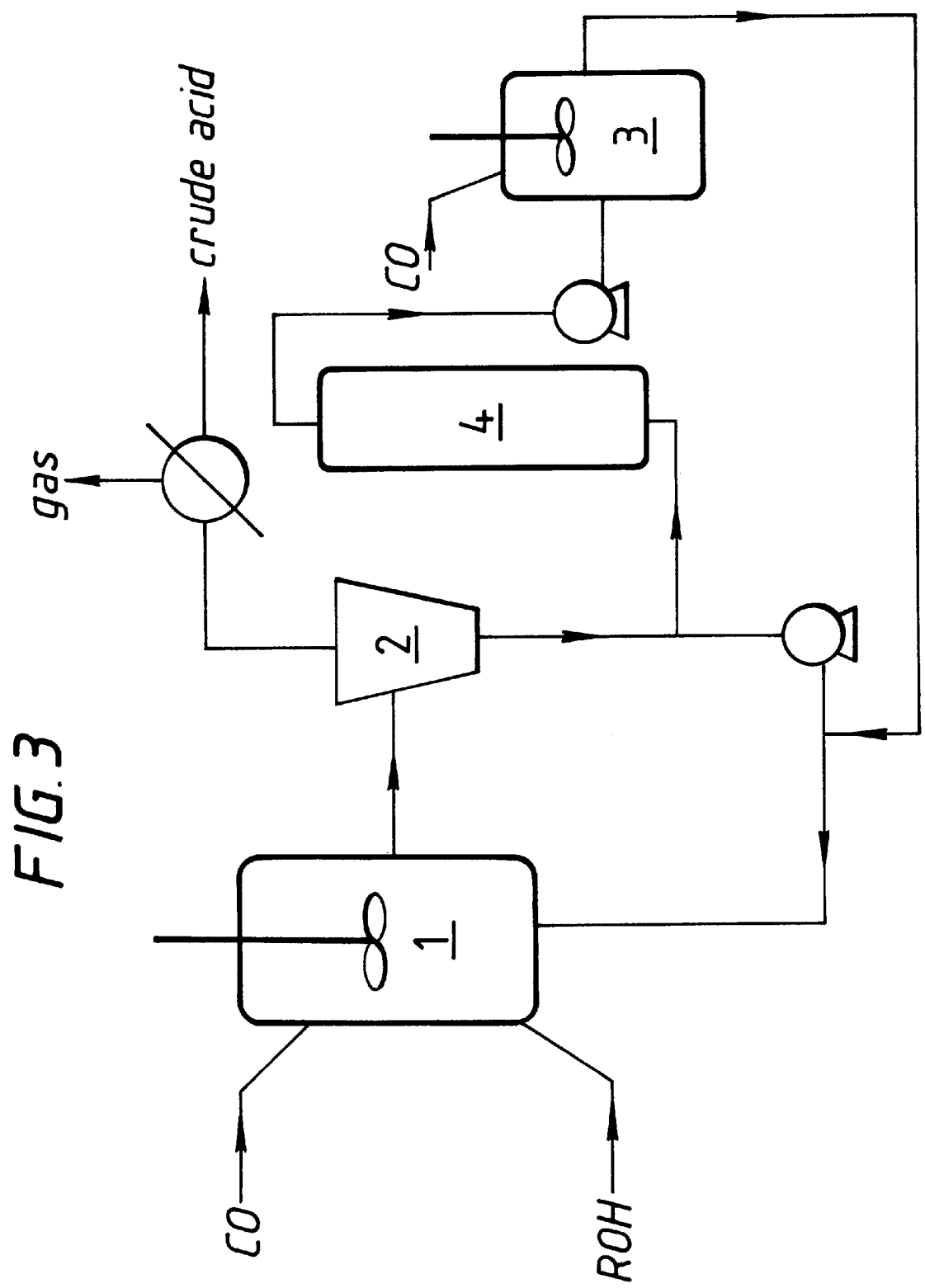
FIG. 3 represents a variant of the foregoing embodiment in which carbon monoxide is dissolved in part of the non-vaporized liquid fraction from the flash unit, after having been first treated on an ion exchange resin.

FIG. 3 describes a variant of the embodiment described in the foregoing diagram. The difference between these two embodiments lies in the fact that the fraction diverted from the recycling loop is treated by being run through a column (4) on an ion exchange resin before the placing in contact with the carbon monoxide.

In each of these two latter diagrams, the diversion of the flow to be placed in contact with the carbon monoxide is effected upstream of the pump for the recycling of the liquid to the reactor. It would not be beyond the scope of the present invention to effect this diversion downstream of this same pump. In a similar manner, for the same two diagrams, the point of contact between the liquid including the dissolved carbon monoxide and that which has not been treated with this gas is situated downstream of the aforesaid pump. Here again it would not be beyond the scope of the present invention to effect this upstream of the pump.

These three diagrams are naturally merely examples of implementing the invention and are not to be regarded as limitations of it.

We claim:

1. Process for the preparation of carboxylic acids which, in a first zone, the reaction in liquid phase is conducted in the presence of a rhodium based catalyst, and in which, in a second zone, the reaction mixture obtained is then partly vaporized; the vaporized fraction, including the carboxylic acid produced, is subsequently purified and the non-vaporized liquid fraction including the catalyst is recycled to the first zone, characterized in that said non-vaporized fraction is placed in contact with carbon monoxide in such a way that said carbon monoxide does not return to the second zone.

2. Process according to claim 1, characterised in that the non-vaporized fraction is recycled to the first zone by means of a pump and that the introduction of the carbon monoxide takes place downstream of said pump.

3. Process according to claim 1, characterised in that the non-vaporized fraction is placed in contract with carbon monoxide dissolved in a liquid flow.

4. Process according to claim 3, characterized in that the liquid flow in which the carbon monoxide is dissolved is a solution which is soluble with the reaction medium.

5. Process according to claim 4, wherein said liquid flow is selected from the group consisting of carboxylic acid, any other reagent employed during the carboxylation reaction and mixtures thereof.

6. Process according to claim 5, characterized in that the liquid flow consists of part of the non-vaporized fraction.

7. Process according to claim 6, which further comprises the step of treating said non-vaporized fraction on an ion exchange resin prior to recycling said fraction to said first zone.

8. Process according to claim 3, characterized in that the amount of carbon monoxide dissolved varies from 0 exclusive to 10%, depending on the temperature and pressure conditions of the liquid.

9. Process according to claim 4, characterised in that the liquid flow in which the carbon monoxide is dissolved includes the catalyst.

10. Process according to claim 4, characterized in that the amount of carbon monoxide dissolved varies from 0 exclusive to 10%.

11. Process according to claim 5, characterised in that the amount of carbon monoxide dissolved varies from 0 exclusive to 10%, depending on the temperature and pressure conditions of the liquid.

12. Process according to claim 6, characterised in that the amount of carbon monoxide dissolved varies from 0 exclusive to 10%, depending on the temperature and pressure conditions of the liquid.

13. Process according to claim 7, characterised in that the amount of carbon monoxide dissolved varies from 0 exclusive to 10%, depending on the temperature and pressure conditions of the liquid.

14. The process of claim 1 wherein alcohol comprises a reactant in said first zone.

\* \* \* \* \*